US007785577B2

(12) United States Patent
Hocquaux et al.

(10) Patent No.: US 7,785,577 B2
(45) Date of Patent: Aug. 31, 2010

(54) PEPTIDES OR PEPTIDIC CONJUGATE DERIVATIVES OF MSH AND THE USE THEREOF FOR COSMETICALLY FIGHTING AGAINST CANITIES

(75) Inventors: Michel Hocquaux, Paris (FR); Anne-Marie Pinel, Toulouse (FR); Jean Martinez, Caux (FR); Gilles Subra, Juvignac (FR)

(73) Assignees: Institut Europeen de Biologie Cellulaiare, Ramonville St. Agne (FR); Centre National de la Recherche Scientifique (CNRS), Paris (FR); Universite de Montpellier I, Montpellier (FR); Universite de Montpellier II, Montpellier (FR)

( * ) Notice: Subject to any disclaimer, the term of this patent is extended or adjusted under 35 U.S.C. 154(b) by 651 days.

(21) Appl. No.: 11/596,288

(22) PCT Filed: May 10, 2005

(86) PCT No.: PCT/FR2005/001166

§ 371 (c)(1),
(2), (4) Date: Nov. 13, 2006

(87) PCT Pub. No.: WO2005/116068

PCT Pub. Date: Dec. 8, 2005

(65) Prior Publication Data

US 2008/0200396 A1  Aug. 21, 2008

(30) Foreign Application Priority Data

May 11, 2004  (FR)  .................................. 04 05069

(51) Int. Cl.
*A61K 8/64*  (2006.01)
(52) U.S. Cl. ........................ 424/70.14; 514/16; 514/17; 514/18
(58) Field of Classification Search ........................ None
See application file for complete search history.

(56) References Cited

U.S. PATENT DOCUMENTS

| | | | |
|---|---|---|---|
| 5,674,839 A | 10/1997 | Hruby et al. | |
| 5,714,576 A * | 2/1998 | Hruby et al. ................ | 530/312 |
| 5,786,332 A | 7/1998 | Girten et al. | |
| 5,830,994 A * | 11/1998 | D'Hinterland et al. ...... | 530/300 |
| 6,245,342 B1 | 6/2001 | Golz-Berner et al. | |
| 6,337,315 B1 | 1/2002 | Mahe et al. | |
| 2005/0187164 A1 | 8/2005 | Pinel | |

FOREIGN PATENT DOCUMENTS

| | | |
|---|---|---|
| EP | 0 669 938 B1 | 9/1995 |
| EP | 0 949 902 B1 | 10/1999 |
| EP | 0 972 522 B1 | 1/2000 |
| WO | WO 01/98362 A2 | 12/2001 |
| WO | WO 02/085925 A2 | 10/2002 |
| WO | WO 03/064458 A2 | 8/2003 |
| WO | WO 03/095474 A2 | 11/2003 |

OTHER PUBLICATIONS

Haskell-Luevano et al., "Truncation Studies of α-Melanotropin Peptides Identify Tripeptide Analogues Exhibiting Prolonged Agonist Bioactivity," Peptides, 1996, 17(6), 995-1002.
Holder et al., "Characterization of aliphatic, cyclic, and aromatic N-terminally 'capped' His-D-Phe-Arg-Trp-$NH_2$ tetrapeptides at the melanocortin receptors," European Journal of Pharmacology, 2003, 462:41-52.
Holder et al., "Structure-Activity Relationships of the Melanocortin Tetrapeptide Ac-His-D-Phe-Arg-Trp-$NH_2$ at the Mouse Melanocortin Receptors. 4. Modifications at the Trp Position," J. Med. Chem., 2002, 45:5736-5744.
Holder et al., "Structure-Activity Relationships of the Melanocortin Tetrapeptide Ac-His-D-Phe-Arg-Trp-$NH_2$ at the Mouse Melanocortic Receptors. 1. Modifications at the His Position," J. Med. Chem., 2002, 45:2801-2810.
Nijenhuis et al., "Discovery and in vivo evaluation of new melanocortin-4 receptor-selective peptides," Peptides, 2003, 24:271-280.
Takahama, Motohide, "α-MSH discovered in primary root of sesame seeds, and trial on remelanization of gray hairs by their extract: immunohistochemical study," Journal of Dermatological Science, Apr. 2004, (34(2), p. 148, XP002302532 & 19th Annual meeting of the Japanese Society for Investigative Dermatology, Kyoto, Japan, Apr. 14-16, 2004, one page.

* cited by examiner

*Primary Examiner*—Christopher R. Tate
*Assistant Examiner*—Roy Teller
(74) *Attorney, Agent, or Firm*—Foley & Lardner LLP

(57) ABSTRACT

The invention relates to a peptide of formula W-DPhe-Arg-Z (I) and to a conjugate thereof of a formula A-W-DPhe-Arg-Z (II), wherein A is a radical corresponding to a monocarboxylic acid of general formula HOOC—R (III), wherein R is an linear or branched possibly substituted by a hydroxy group aliphatic $C_1$-$C_{24}$ radical which can comprise one or several unsaturations, preferably from 1 to 6 unsaturations, a lipoic acid or the reduced form thereof, a dihydrolipoic acid, N-lipoyl-lysine or a phenylbutyric acid, W is His, Ala-His, Ala-Ala-His, Nle-Ala-His, DTrp-Ala-His, Nle-Trp-His, Lys, Ala-Lys, Nle-Ala-Lys, Orn, Ala-Orn, Nle-Ala-Orn, Ala, Nle-Ala-Ala, Arg, Ala-Arg. Nle-Ala-Arg, Nle-Ala-DTrp or a bond in case of compounds of formula (II), Z is $NH_2$, OH and OR, wherein R is a linear or branched aliphatic $C_1$-$C_{24}$ radical, Trp$NH_2$, Nap$NH_2$, Tpi$NH_2$, Tic$NH_2$, AlaNH2, TrpOH, NapOH, TpiOH, TicOH, AlaOH, PheN$H_2$, or PheOH, exempting a peptidic conjugate for which A is a radical corresponding to an acetic acid, W is Nle-Ala-His and Z is Trp$NH_2$ in the form of enantiomers or diastereoisomer and the mixtures thereof including racemic mixtures. The use of the inventive compounds for cosmetically fighting against canities is also disclosed.

10 Claims, No Drawings

PEPTIDES OR PEPTIDIC CONJUGATE DERIVATIVES OF MSH AND THE USE THEREOF FOR COSMETICALLY FIGHTING AGAINST CANITIES

This application is a National Stage application of PCT/FR2005/001166, filed May 10, 2005, which claims priority from French patent application FR 0405069, filed May 11, 2004. The entire contents of each of the aforementioned applications are incorporated herein by reference.:

The invention relates to new peptides or peptidic conjugate derivatives of MSH and their use in the cosmetic treatment of canities or to help prevent greying hair.

Hair colour is determined by the concentration in the keratinocytes of melanin produced by the melanocytes. Hair pigmentation requires the presence of melanocytes in the bulb of the hair follicle. Melanocytes are specialized cells which synthesize melanin. Two groups of melanin pigment are produced: the eumelanins and the phaeolmelanins. These pigments are transmitted to the keratinocytes which make up the hair shaft. Melanin synthesis, or melanogenesis, involves tyrosine which is transformed into melanin under the effect of tyrosinase. Tyrosinase is the principal enzyme involved in this cascade reaction.

Along with the appearance of wrinkles, greying hair is one of the first signs of ageing. There are many reasons for hair turning grey but the underlying interactions are very poorly understood: genetic factors, ageing process, environment, lifestyle. Many hypotheses have been put forward to explain the ageing process. The appearance of grey hair is therefore related to:

1. A reduction in the number of melanocytes in the hair bulb.
2. A reduction in the amount of melanin in the hair shaft.

Biochemical colouration elements are present but inactive: the production and transport of melanin gradually stops.

3. A defect in the transfer of melanin from the melanosomes found in the keratinocytes. The production of melanin in the hair follicles takes place just above the dermal papilla. This is where the transfer of melanin to the keratinocyte occurs, giving rise to the hair shaft.

This invention relates to peptides and peptidic conjugate derivatives of MSH.

MSH, or Melanocyte Stimulating Hormone, is the hormone responsible for pigmentation and is a highly important regulator in melanogenesis. (*Exp. Dermatol.* 1998/07/43-150). MSH triggers melanocyte proliferation and melanin synthesis.

This invention is based on research into peptidic structures which activate melanogenesis inside the melanocytes within the hair bulb.

The applicant has made the surprising discovery that new peptides and peptidic conjugates containing at least 6 amino acids and including the sequence DPhe-Arg have a substantial activating effect on melanogenesis in the melanocytes of the hair bulb.

Patent application EP 669 938 describes peptide sequences containing at least the sequence His-Phe-Arg. However, phenylalanine can be found in either its D or L form. Moreover, it is specified that Phe advantageously represents homoPhe or p-fluoroPhe. In addition, in the examples given, only D.homoPhe is used. It is also specified that the presence of D.homoPhe is very important in the stimulation of melanogenesis and the activation of tyrosinase. Finally, this document does not suggest that these peptides have a melanogenesis activating effect on the melanocytes of the hair bulb or that they can be used to treat canities or to help prevent greying hair.

Patent application WO 03/064458 describes peptidic conjugates of formula R—V-Ala-His-X—Y-Trp-NH$_2$ (SEQ ID NO: 1) in which X can represent phenylalanine in the D or L form, Y represents arginine and A an acyl group.

Thus the peptide Ac-Nle-Ala-His-DPhe-Arg-Trp-NH$_2$ is described.

However, these peptidic conjugates necessarily start with the sequence Nle-Ala-His and end with the sequence Trp-NH$_2$. In addition, X and Y can represent other amino acids such as phenylalanine or arginine. Moreover, peptides or peptidic conjugates according to this invention have a greater effect on melanogenesis compared to the peptide Ac-Nle-Ala-His-DPhe-Arg-Trp-NH$_2$.

U.S. Pat. No. 5,714,576 describes linear fragment analogues of MSH that can, among other things, stimulate melanogenesis. Nevertheless, the tests described were performed only on frogs. In addition, these fragments contain at least 7 amino acids rather than 6 at the most, as is the case for this invention. Moreover, this document does not suggest that smaller fragments might have an effect on melanogenesis. In addition, when the fragments described in the document contain the sequence His-DPhe-Arg-Trp, an amino acid is always present after Trp and these sequences never contain a final Trp-NH$_2$ amino acid, which is not the case in this invention.

This invention therefore relates to a peptide of formula (I)

W-DPhe-Arg-Z    (I)

or its peptidic conjugate of formula (II)

A-W-DPhe-Arg-Z    (II)

wherein:

A represents a radical corresponding to a monocarboxylic acid of general formula (III)

HOOC—R    (III)

wherein R represents a linear or branched aliphatic C$_1$-C$_{24}$ radical, possibly substituted with a hydroxy group, and which may contain one or several unsaturations, advantageously 1 to 6 unsaturations.

lipoic acid or its reduced form dihydrolipoic acid, N-lipoyl-lysine or phenylbutyric acid;

W represents His, Ala-His, Ala-Ala-His, Nle-Ala-His, DTrp-Ala-His, Nle-Trp-His, Lys, Ala-Lys, Nle-Ala-Lys, Orn, Ala-Orn, Nle-Ala-Orn, Ala, Nle-Ala-Ala, Arg, Ala-Arg, Nle-Ala-Arg, Nle-Ala-DTrp or a bond in the case of peptidic conjugates of formula II;

Z represents NH$_2$, OH, OR1 wherein R1 represents a linear or branched aliphatic C$_1$-C$_{24}$ radical, TrpNH$_2$, NapNH$_2$, TpiNH$_2$, TicNH$_2$, AlaNH$_2$, TrpOH, NapOH, TpiOH, TicOH, AlaOH, PheNH$_2$ or PheOH;

with the exception of a peptidic conjugate for which A is a radical corresponding to an acetic acid, W is Nle-Ala-His and Z represents Trp NH$_2$;

in the form of enantiomers or diastereoisomers as well as mixtures thereof, including racemic mixtures.

Amino acids in the peptide of formula (I) or its peptidic derivative of formula (II) can have a D, L or DL configuration if this is not otherwise specified.

Thus peptides of formula (I) or their peptidic derivatives of formula (II) can include one or more asymmetrical carbon atoms. They can therefore occur in the form of enantiomers or diastereoisomers. These enantiomers and diastereoisomers, as well as their mixtures, constitute part of the invention.

The peptidic conjugates of formula (II) are low molecular weight derivatives which are obtained in the form of amides of the compound of formula (III).

In addition, peptides of formula (I) and peptidic conjugates of formula (II) can be coupled to zinc in the form of a salt in order to form complexes.

Within the scope of this invention, the following abbreviations are used:
Lys, lysine,
Arg, arginine,
Trp, tryptophan,
Nap, naphthylalanine,
Tpi, tetrahydronorhaman-3 carboxylic acid,
Tic, tetrahydroisoquinoline-3 carboxylic acid
Ala, Alanine,
Phe, phenylalanine,
Nle, Norleucine,
His, histidine,
Orn, ornithine.

It is also pointed out that the peptides and peptidic conjugates mentioned above and being the object of this invention can be obtained in a terminal $NH_2$ form (in other words, with an amide group) or in a terminal OH form (in other words, with a carboxylic group).

Advantageously, the acid of formula (III) is a polyunsaturated acid, that is to say having 1 to 6 unsaturations. Preferentially, it is an omega-3 acid.

The omega-3 acids include α-linoleic acid, cervonic acid, timnodonic acid and pinolenic acid. Cervonic, timnodonic and pinolenic acids are also known by the following designations 4,7,10,13,16,19-docohexanoic acid (DHA), 5,8,11,14,17-eicosapentaenoic acid (EPA) and 5,9,12-octodecatrienic acid.

When A is a monocarboxylic acid of general formula (III), it is advantageously chosen from among acetic acid, myristic acid, palmitic acid, hydroxydecanoic acid and decanoic acid and notably trans-10-hydroxy-Δ2-decanoic acid and trans-oxo-9-decene-2-oic acid.

Advantageously, the acid of formula (III) is an acid chosen from among lipoic acid or its reduced form dihydrolipoic acid, N-lipoyl-lysine or phenylbutyric acid.

Peptidic conjugates whereby A is chosen from among lipoic acid and acetic acid are particularly suitable within the scope of this invention.

Advantageously, the peptidic conjugates of general formula (II) are such that A has the definition given above, W represents His, Ala-His, Ala-Ala-His, DTrp-Ala-His, Nle-Trp-His, Lys, Ala-Lys, Nle-Ala-Lys, Orn, Ala-Orn, Nle-Ala-Orn, Ala, Nle-Ala-Ala, Arg, Ala-Arg, Nle-Ala-Arg, Nle-Ala-DTrp or a bond and Z represents $NH_2$, OH, OR1 wherein R1 represents a linear or branched aliphatic $C_1$-$C_{24}$ radical, $TrpNH_2$, $NapNH_2$, $TpiNH_2$, $TicNH_2$, $AlaNH_2$, TrpOH, NapOH, TpiOH, TicOH, AlaOH, $PheNH_2$ or PheOH;

or W represents Nle-Ala-His and Z represents $NH_2$, OH, OR wherein R represents a linear or branched aliphatic $C_1$-$C_{24}$ radical, $NapNH_2$, $TpiNH_2$, $TicNH_2$, $AlaNH_2$, TrpOH, NapOH, TpiOH, TicOH, AlaOH, $PheNH_2$ or PheOH.

Advantageously, the peptides or peptidic conjugates according to the invention contain 4 amino acids at the most.

Among the peptidic conjugates of the invention, peptidic conjugates having the following formulae can be cited:

```
a-A-Nle-Ala-His-DPhe-Arg-Trp-NH2
b-A-Nle-Ala-Lys-DPhe-Arg-Trp-NH2
c-A-Nle-Ala-Arg-DPhe-Arg-Trp-NH2
d-A-Nle-Ala-Orn-DPhe-Arg-Trp-NH2
e-A-Nle-Ala-DTrp-DPhe-Arg-Trp-NH2
f-A-Nle-Ala-Ala-DPhe-Arg-Trp-NH2
g-A-Ala-Ala-His-DPhe-Arg-Trp-NH2
h-A-DTrp-Ala-His-DPhe-Arg-Trp-NH2
i-A-Nle-Ala-His-DPhe-Arg-Nap-NH2
j-A-Nle-Ala-His-DPhe-Arg-Phe-NH2
k-A-Nle-Ala-His-DPhe-Arg-Ala-NH2
l-A-Nle-Ala-His-DPhe-Arg-Tpi-NH2
m-A-Nle-Ala-His-DPhe-Arg-Tic-NH2
n-A-Nle-Ala-His-DPhe-Arg-NH2
o-A-Nle-Trp-His-DPhe-Arg-Trp-NH2
p-A-Ala-His-DPhe-Arg-Trp-NH2
q-A-His-DPhe-Arg-Trp-NH2
r-A-His-DPhe-Arg-Phe-NH2
s-A-His-DPhe-Arg-Ala-NH2
t-A-Lys-DPhe-Arg-Trp-NH2
u-A-DPhe-Arg-Trp-NH2
v-A-His-PDhe-Arg-NH2
w-A-DPhe-Arg-NH2
``` wherein A has the definition given above on condition that in the case of conjugates of formula a, A does not represent a radical corresponding to acetic acid.

Among the peptidic conjugates of the invention, the following peptidic conjugates can be cited:

```
1-Ac-Nle-Ala-Lys-DPhe-Arg-Trp-NH2
2-Ac-Nle-Ala-Arg-DPhe-Arg-Trp-NH2
3-Ac-Nle-Ala-Orn-DPhe-Arg-Trp-NH2
4-Ac-Nle-Ala-DTrp-DPhe-Arg-Trp-NH2
5-Ac-Nle-Ala-Ala-DPhe-Arg-Trp-NH2
6-Ac-Ala-Ala-His-DPhe-Arg-Trp-NH2
7-Ac-DTrp-Ala-His-DPhe-Arg-Trp-NH2
8-Prop-Nle-Ala-His-DPhe-Arg-Trp-NH2
9-But-Nle-Ala-His-DPhe-Arg-Trp-NH2
10-Palm-Nle-Ala-His-DPhe-Arg-Trp-NH2
11-Lip-Nle-Ala-His-DPhe-Arg-Trp-NH2
12-Pbu-Nle-Ala-His-DPhe-Arg-Trp-NH2
13-Palm-Nle-Ala-His-DPhe-Arg-Trp-NH2
14-Ac-Nle-Ala-His-DPhe-Arg-Nap-NH2
15-Ac-Nle-Ala-His-DPhe-Arg-Phe-NH2
16-Ac-Nle-Ala-His-DPhe-Arg-Ala-NH2
```

```
-continued
17-Ac-Nle-Ala-His-DPhe-Arg-Tpi-NH2

18-Ac-Nle-Ala-His-DPhe-Arg-Tic-NH2

19-Ac-Nle-Ala-His-DPhe-Arg-NH2

20-Ac-Nle-Trp-His-DPhe-Arg-Trp-NH2

21-Hex-Ala-His-DPhe-Arg-Trp-NH2

22-Palm-His-DPhe-Arg-Trp-NH2

23-Palm-His-DPhe-Arg-Phe-NH2

24-Palm-His-DPhe-Arg-Ala-NH2

25-Pbu-His-DPhe-Arg-Trp-NH2

26-Lip-His-DPhe-Arg-Trp-NH2

27-Lip-Lys-DPhe-Arg-Trp-NH2

28-Palm-DPhe-Arg-Trp-NH2

29-Pbu-DPhe-Arg-Trp-NH2

30-Lip-DPhe-Arg-Trp-NH2

31-Palm-His-DPhe-Arg-NH2

32-Pbu-His-DPhe-Arg-NH2

33-Lip-His-DPhe-Arg-NH2

34-Palm-DPhe-Arg-NH2

35-Pbu-DPhe-Arg-NH2

36-Lip-DPhe-Arg-NH2
```

The peptidic conjugates according to this invention can be advantageously obtained either by conventional chemical synthesis or by enzymatic synthesis, according to whatever procedures are known to the man skilled in the art.

The peptides or their peptidic conjugates can be administered for cosmetic use by topical route. They can also be used as food supplements, in other words in the nutraceutical field, by oral route.

The peptidic conjugates according to the invention are preferably administered by topical route.

According to another aspect, this invention also covers a cosmetic, dermatological or pharmaceutical composition or even food supplement containing a peptide or peptidic conjugate according to this invention.

The cosmetic or dermatological composition can be advantageously applied to the entire scalp.

The cosmetic or dermatological composition can, for example, be in the form of lotions, treatment shampoos, sprays, conditioners, creams, ointments, solutions, emulsions, gels, milks, masks and serums.

In the topical cosmetic composition, the peptide conjugate or peptide according to the invention can be present at a concentration between $10^{-8}$ M and $10^{-3}$ M, preferably between $10^{-7}$ M and $10^{-5}$ M.

Finally, another object of this invention relates to a cosmetic treatment process to help prevent greying hair and/or for the treatment of canities and involves application to the scalp of a composition containing a peptide or peptidic conjugate of the invention or even administration by oral route of a food supplement containing a peptide or peptidic conjugate of the invention.

Cosmetic compositions according to this invention for topical application to the scalp can also include a UVB filter providing protection of the scalp against the sun. The following are suitable UVB filters (INCI names):

p-aminobenzoic acid or PABA and its esters:
    EthylhexyldimethylPABA
    PEG-25PABA Cinnamates:
    Ethylhexyl Methoxycinnamate
    Isoamyl p-Methoxycinnamate
    Octocrylene Salicylates:
    Homosalate
    Ethylhexyl Salicylate Benzimidazoles:
    Phenylbenzimidazole sulfonic acid Benzylidene Camphor derivatives:
    4-Methylbenzylidene Camphor
    Benzilidene Camphor
    Camphor Benzalkonium Methosulphate
    Polyacrylamidomethyl Benzylidene Camphor Triazines:
    Ethylhexyl Triazone
    Diethylhexyl Butamido Triazone.

The peptides of the invention have undergone pharmacological tests which demonstrate their effectiveness in the treatment of canities. The following non-limiting examples are given for the purpose of information.

EXAMPLE 1

Activity of Various Peptides in a Melanogenesis Stimulation Test

Test: Study of the quantification of a second messenger: cAMP

α-MSH has a receptor in the skin, melanocortin-1 receptor MC1r. When an agonist binds to this receptor, it leads to activation of a molecule, adenylate cyclase, which produces cAMP. Quantifying cAMP makes it possible to evaluate the affinity of a ligand for its receptor.

Protocol: The cells used to test MC1r were human melanocytes. The peptides were tested at concentrations of $10^{-6}$ to $10^{-11}$ M. The reference molecule, α-MSH, was tested at the same concentrations.

$EC_{50}$ is the ligand concentration giving 50% of maximum stimulation. The $EC_{50}$ values reported in the table below are given in nM and correspond to the mean of 3 tests.

| Peptidic conjugate | EC50 |
|---|---|
| Alpha-MSH | 8.50 |
| Prior art peptide | 1.8 |
| Conjugate no. 2 | 0.6 |
| Conjugate no. 8 | 1 |
| Conjugate no. 13 | 1.6 |

The peptides of the invention have an activity that is superior to that of alpha-MSH.

EXAMPLE 2

Lotion Containing Peptidic Conjugate 11

|  | In g |
| --- | --- |
| Peptidic conjugate 11 | $20 \cdot 10^{-6}$ |
| 95° ethanol | 60 |
| Propylene glycol | 10 |
| water/Preservatives | qs for 100 |

EXAMPLE 3

Lotion Containing Peptidic Conjugate 24

|  | In g |
| --- | --- |
| Peptidic conjugate 24 | $20 \cdot 10^{-6}$ |
| Water | 81 |
| Keltrol ® T | 0.5 |
| (xanthane gum sold by KECCO) | |
| Techpolymer MB-4C | 1 |
| (polymethyl methacrylate) | |
| Sold by Sekisui | |
| Sepigel ® 305 | 0.5 |
| (Polyacrylamide/$C_{13}$-$C_{14}$ Isoparaffin/ | |
| Laureth-7 Sold by SEPPIC) | |
| Silicon oil | 2 |
| Butylene glycol | 5 |

Two applications per day (morning and night) for 3 months of the lotion described in example 2 to a totally grey-haired woman made it possible to visualize the appearance of repigmented black hair.

The invention claimed is:

1. Method for the cosmetic treatment of canities comprising the administration to a patient in need thereof of an effective amount of a peptide of formula (I)

$$W\text{-DPhe-Arg-Z} \qquad (I)$$

or its peptidic conjugate of formula (II)

$$A\text{-W-DPhe-Arg-Z} \qquad (II)$$

wherein:
A represents a radical corresponding to
a monocarboxylic acid of general formula (III)

$$\text{HOOC—R} \qquad (III)$$

wherein R represents a linear or branched aliphatic $C_1$-$C_{24}$ radical, possibly substituted with a hydroxy group, and which may contain one or several unsaturations.
lipoic acid or its reduced form dihydrolipoic acid, N-lipoyl-lysine or phenylbutyric acid
W represents His, Ala-His, Ala-Ala-His, Nle-Ala-His, DTrp-Ala-His, Nle-Trp-His, Lys, Ala-Lys, Nle-Ala-Lys, Orn, Ala-Orn, Nle-Ala-Orn, Ala, Nle-Ala-Ala, Arg, Ala-Arg, Nle-Ala-Arg, Nle-Ala-DTrp or a bond in the case of peptidic conjugates of formula II
Z represents $NH_2$, OH, OR1 wherein R1 represents a linear or branched aliphatic $C_1$-$C_{24}$ radical, $TrpNH_2$, $NapNH_2$, $TpiNH_2$, $TicNH_2$, $AlaNH_2$, TrpOH, NapOH, TpiOH, TicOH, AlaOH, $PheNH_2$ or PheOH
with the exception of a peptidic conjugate for which A is a radical corresponding to an acetic acid, W is Nle-Ala-His and Z represents Trp $NH_2$,
in the form of enantiomers or diastereoisomers as well as mixtures thereof, including racemic mixtures,
and wherein the peptide of formula (I) and peptidic conjugate of formula (II) each contains at most six amino acids.

2. The method as claimed in claim 1 wherein the acid of general formula (III) is an omega-3 acid chosen from among alpha-linoleic acid, cervonic acid, timnodonic acid or pinolenic acid or an aliphatic $C_1$-$C_{24}$ acid chosen from among acetic acid, myristic acid, palmitic acid or the hydroxyde-

SEQUENCE LISTING

```
<160> NUMBER OF SEQ ID NOS: 1

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Norleucine, norvaline or 2-N-Me-norleucine
<220> FEATURE:
<221> NAME/KEY: MOD_RES
<222> LOCATION: (4)..(4)
<223> OTHER INFORMATION: D- or L-Phe

<400> SEQUENCE: 1

Xaa Ala His Phe Arg Trp
1               5
``` cenoic and decenoic acid or an acid chosen from among lipoic acid or its reduced form dihydrolipoic acid, N-lipoyl-lysine or phenylbutyric acid.

3. The method as claimed in claim 1 wherein A is chosen from among radicals corresponding to lipoic acid and acetic acid.

4. The method as claimed in claim 1, wherein the peptidic conjugate is chosen from among peptidic compounds having the following formulae:

a) A-Nle-Ala-His-Dphe-Arg-Trp-NH2;
b) A-Nle-Ala-Lys-Dphe-Arg-Trp-NH2;
c) A-Nle-Ala-Arg-Dphe-Arg-Trp-NH2;
d) A-Nle-Ala-Orn-Dphe-Arg-Trp-NH2;
e) A-Nle-Ala-DTrp-Dphe-Arg-Trp-NH2;
f) A-Nle-Ala-Ala-Dphe-Arg-Trp-NH2;
g) A-Ala-Ala-His-Dphe-Arg-Trp-NH2;
h) A-DTrp-Ala-His-Dphe-Arg-Trp-NH2;
i) A-Nle-Ala-His-DPhe-Arg-Nap-NH2;
j) A-Nle-Ala-His-DPhe-Arg-Phe-NH2;
k) A-Nle-Ala-His-DPhe-Arg-Ala-NH2;
l) A-Nle-Ala-His-DPhe-Arg-Tpi-NH2;
m) A-Nle-Ala-His-DPhe-Arg-Tic-NH2;
n) A-Nle-Ala-His-DPhe-Arg-NH2;
o) A-Nle-Ala-His-DPhe-Arg-Trp-NH2;
p) A-Ala-His-DPhe-Arg-Trp-NH2;
q) A-His-DPhe-Arg-Trp-NH2;
r) A-His-DPhe-Arg-Phe-NH2;
s) A-His-DPhe-Arg-Ala-NH2;
t) A-Lys-DPhe-Arg-Trp-NH2;
u) A-DPhe-Arg-Trp-NH2;
v) A-His-DPhe-Arg-NH2; and
w) A-DPhe-Arg-NH2;

wherein A has the definition given above on condition that in the case of conjugates of formula a, A does not represent a radical corresponding to acetic acid.

5. The method as claimed in claim 4, wherein the peptidic conjugate is chosen from among:

a) Ac-Nle-Ala-Lys-DPhe-Arg-Trp-NH2;
b) Ac-Nle-Ala-Arg-DPhe-Arg-Trp-NH2;
c) Ac-Nle-Ala-Orn-DPhe-Arg-Trp-NH2;
d) Ac-Nle-Ala-DTrp-DPhe-Arg-Trp-NH2;
e) Ac-Nle-Ala-Ala-DPhe-Arg-Trp-NH2;
f) Ac-Ala-Ala-His-Dphe-Arg-Trp-NH2;
g) Ac-DTrp-Ala-His-DPhe-Arg-Trp-NH2;

-continued h) Prop-Nle-Ala-His-DPhe-Arg-Trp-NH2;
i) But-Nle-Ala-His-DPhe-Arg-Trp-NH2;
j) Palm-Nle-Ala-His-DPhe-Arg-Trp-NH2;
k) Lip-Nle-Ala-His-DPhe-Arg-Trp-NH2;
l) Pbu-Nle-Ala-His-DPhe-Arg-Trp-NH2;
m) Palm-Nle-Ala-His-DPhe-Arg-Trp-NH2;
n) Ac-Nle-Ala-His-DPhe-Arg-Nap-NH2;
o) Ac-Nle-Ala-His-DPhe-Arg-Phe-NH2;
p) Ac-Nle-Ala-His-DPhe-Arg-Ala-NH2;
q) Ac-Nle-Ala-His-DPhe-Arg-Tpi-NH2;
r) Ac-Nle-Ala-His-DPhe-Arg-Tic-NH2;
s) Ac-Nle-Ala-His-DPhe-Arg-NH2;
t) Ac-Nle-Trp-His-DPhe-Arg-Trp-NH2;
u) Hex-Ala-His-DPhe-Arg-Trp-NH2;
v) Palm-His-DPhe-Arg-Trp-NH2;
w) Palm-His-DPhe-Arg-Phe-NH2;
x) Palm-His-DPhe-Arg-Ala-NH2;
y) Pbu-His-DPhe-Arg-Trp-NH2;
z) Lip-His-DPhe-Arg-Trp-NH2;
aa) Lip-Lys-DPhe-Arg-Trp-NH2;
bb) Palm-DPhe-Arg-Trp-NH2;
cc) Pbu-DPhe-Arg-Trp-NH2;
dd) Lip-DPhe-Arg-Trp-NH2;
ee) Palm-His-DPhe-Arg-NH2;
ff) Pbu-His-DPhe-Arg-NH2;
gg) Lip-His-DPhe-Arg-NH2;
hh) Palm-DPhe-Arg-NH2;
ii) Pbu-DPhe-Arg-NH2; and
jj) Lip-DPhe-Arg-NH2;

wherein Lip is lipoic acid, and Palm is palmitic acid.

6. The method as claimed in claim 1 consisting of the application to the scalp of a cosmetic composition containing a peptide of formula (I) or peptidic conjugate of formula (II) as defined in claim 1.

7. The method as claimed in claim 1 consisting of the administration by oral route of a food supplement containing a peptide of formula (I) or peptidic conjugate of formula (II) as defined in claim 1.

8. Peptidic conjugate chosen from among:

a) Ac-Nle-Ala-Lys-DPhe-Arg-Trp-NH2;
b) Ac-Nle-Ala-Arg-DPhe-Arg-Trp-NH2;
c) Ac-Nle-Ala-Orn-DPhe-Arg-Trp-NH2;
d) Ac-Nle-Ala-DTrp-DPhe-Arg-Trp-NH2;

-continued

| | |
|---|---|
| e) | Ac-Nle-Ala-Ala-DPhe-Arg-Trp-NH2; |
| f) | Ac-Ala-Ala-His-Dphe-Arg-Trp-NH2; |
| g) | Ac-DTrp-Ala-His-DPhe-Arg-Trp-NH2; |
| h) | Prop-Nle-Ala-His-DPhe-Arg-Trp-NH2; |
| i) | But-Nle-Ala-His-DPhe-Arg-Trp-NH2; |
| j) | Palm-Nle-Ala-His-DPhe-Arg-Trp-NH2; |
| k) | Lip-Nle-Ala-His-DPhe-Arg-Trp-NH2; |
| l) | Pbu-Nle-Ala-His-DPhe-Arg-Trp-NH2; |
| m) | Palm-Nle-Ala-His-DPhe-Arg-Trp-NH2; |
| n) | Ac-Nle-Ala-His-DPhe-Arg-Nap-NH2; |
| o) | Ac-Nle-Ala-His-DPhe-Arg-Phe-NH2; |
| p) | Ac-Nle-Ala-His-DPhe-Arg-Ala-NH2; |
| q) | Ac-Nle-Ala-His-DPhe-Arg-Tpi-NH2; |
| r) | Ac-Nle-Ala-His-DPhe-Arg-Tic-NH2; |
| s) | Ac-Nle-Ala-His-DPhe-Arg-NH2; |
| t) | Ac-Nle-Trp-His-DPhe-Arg-Trp-NH2; |
| u) | Hex-Ala-His-DPhe-Arg-Trp-NH2; |
| v) | Palm-His-DPhe-Arg-Trp-NH2; |
| w) | Palm-His-DPhe-Arg-Phe-NH2; |

-continued

| | |
|---|---|
| x) | Palm-His-DPhe-Arg-Ala-NH2; |
| y) | Pbu-His-DPhe-Arg-Trp-NH2; |
| z) | Lip-His-DPhe-Arg-Trp-NH2; |
| aa) | Lip-Lys-DPhe-Arg-Trp-NH2; |
| bb) | Palm-DPhe-Arg-Trp-NH2; |
| cc) | Pbu-DPhe-Arg-Trp-NH2; |
| dd) | Lip-DPhe-Arg-Trp-NH2; |
| ee) | Palm-His-DPhe-Arg-NH2; |
| ff) | Pbu-His-DPhe-Arg-NH2; |
| gg) | Lip-His-DPhe-Arg-NH2; |
| hh) | Palm-DPhe-Arg-NH2; |
| ii) | Pbu-DPhe-Arg-NH2; and |
| jj) | Lip-DPhe-Arg-NH2; | wherein Lip is lipoic acid, and Palm is palmitic acid.

9. The method as claimed in claim 1, wherein R represents a linear or branched aliphatic $C_1$-$C_{24}$ radical, possibly substituted with a hydroxy group, and which contains 1 to 6 unsaturations.

10. The method as claimed in claim 2, wherein the acid of general formula (III) is a decenoic acid chosen from trans-10-hydroxy-$\Delta$2-decenoic acid and trans-oxo-9-decene-2-oic acid.

* * * * *